(12) United States Patent
Sakotic et al.

(10) Patent No.: US 11,510,822 B2
(45) Date of Patent: Nov. 29, 2022

(54) HEEL PATCH

(71) Applicant: EUROMED, INC., Orangeburg, NY (US)

(72) Inventors: Ljiljana Sakotic, Greenwood Lake, NY (US); Matthew J. Clemente, Glen Rock, NJ (US); Nohora Cárdenas, New Milford, NJ (US)

(73) Assignee: EUROMED, INC., Orangeburg, NY (US)

( * ) Notice: Subject to any disclaimer, the term of this patent is extended or adjusted under 35 U.S.C. 154(b) by 714 days.

(21) Appl. No.: 16/474,821

(22) PCT Filed: Dec. 29, 2017

(86) PCT No.: PCT/US2017/069016
§ 371 (c)(1),
(2) Date: Jun. 28, 2019

(87) PCT Pub. No.: WO2018/126174
PCT Pub. Date: Jul. 5, 2018

(65) Prior Publication Data
US 2020/0121515 A1 Apr. 23, 2020

Related U.S. Application Data

(60) Provisional application No. 62/440,952, filed on Dec. 30, 2016.

(51) Int. Cl.
*A61F 13/02* (2006.01)
*A61F 13/06* (2006.01)
*A61F 13/00* (2006.01)
*A61K 8/02* (2006.01)
*A61K 8/31* (2006.01)
(Continued)

(52) U.S. Cl.
CPC ...... *A61F 13/067* (2013.01); *A61F 13/00063* (2013.01); *A61K 8/0208* (2013.01); *A61K 8/31* (2013.01); *A61K 8/368* (2013.01); *A61K 8/42* (2013.01); *A61K 8/731* (2013.01);
(Continued)

(58) Field of Classification Search
CPC .............. A61F 13/0359; A61F 13/0253; A61F 13/0246; A61F 13/0226; A61F 13/023; A61F 13/02; A61F 13/0243; A61F 13/00076; A61F 13/0266; A61F 2013/00089; A61F 13/00; A61F 13/067; A61F 13/00063; A61F 13/0259;
(Continued)

(56) References Cited

U.S. PATENT DOCUMENTS 6,159,497 A 12/2000 LaPrade et al.
6,495,158 B1 12/2002 Buseman et al.
(Continued)

FOREIGN PATENT DOCUMENTS

WO 0239940 A1 5/2002

OTHER PUBLICATIONS

International Search Report dated Mar. 9, 2018, in PCT/US2017/069016 (5 pages).

*Primary Examiner* — Eisa B Elhilo
(74) *Attorney, Agent, or Firm* — Bookoff McAndrews, PLLC

(57) ABSTRACT

An improved therapeutic adhesive patch for application to the heel is described for treating or preventing heel disorders or conditions, such as cracked heel.

20 Claims, 5 Drawing Sheets

(51) Int. Cl.
    *A61K 8/368*     (2006.01)
    *A61K 8/42*     (2006.01)
    *A61K 8/73*     (2006.01)
    *A61K 8/81*     (2006.01)
    *A61K 8/92*     (2006.01)
    *A61Q 19/00*     (2006.01)

(52) U.S. Cl.
    CPC .............. *A61K 8/8117* (2013.01); *A61K 8/92* (2013.01); *A61Q 19/007* (2013.01)

(58) Field of Classification Search
    CPC ........ A61K 8/0208; A61K 8/368; A61K 8/42; A61K 8/92
    USPC .............................................. 424/447; 602/48
    See application file for complete search history.

(56) References Cited

U.S. PATENT DOCUMENTS

| | | | |
|---|---|---|---|
| 7,189,410 B1* | 3/2007 | Drohan | A61K 31/43 514/3.3 |
| 9,078,948 B2 | 7/2015 | Jensen et al. | |
| 2009/0065014 A1* | 3/2009 | Nagata | A61F 13/067 132/73 |
| 2011/0105977 A1 | 5/2011 | Hart | |
| 2013/0152944 A1* | 6/2013 | Okada | A61F 13/024 606/204.15 |

\* cited by examiner

HEEL PATCH

CROSS-REFERENCE TO RELATED APPLICATIONS

This application is the § 371 national stage entry of International Application No. PCT/US2017/069016 filed on Dec. 29, 2017, which claims the benefit of priority to U.S. Provisional Application No. 62/440,952 filed on Dec. 30, 2016.

TECHNICAL FIELD

The present invention relates to an improved therapeutic adhesive patch for application to the heel for the prevention and/or treatment of various disorders or conditions of the heel. The configuration of the patch promotes rapid application of the patch to the heel with the assurance of a sustained and superior fit.

BACKGROUND

Cracked heels are a common problem that primarily affect adults and the elderly and that may develop into fissures, fungal infections and ulcerations if left untreated. Problems that may contribute to heel fissures include, but are not limited to, age, diabetes, psoriasis, obesity, athlete's foot, eczema, prolonged standing, kidney disease, ill-fitting shoes and residing in a dry climate.

One of the first signs of cracked heels is the formation of thick, discolored callus tissue that may result in pain with common pressure-related activities like walking or running. If the callus is untreated and subjected to continuous pressure, small and/or deep breaks may occur, which leads to bleeding and possible infection.

A need therefore exists for an improved method for effectively and conveniently treating skin on the heel of a foot of a mammal in need thereof. The present invention addresses this need by providing a uniquely structured adhesive heel patch with a primary release liner that results in the rapid and consistently accurate positioning of the heel patch with minimal problems that is wearable over an extended period of time in the presence or absence of different types of footwear.

SUMMARY OF THE INVENTION

An aspect of the present invention is a flexible adhesive patch arrangement comprising: a flexible adhesive patch comprising: a backing having two sides; a therapeutic adhesive composition coated on at least a portion of one side of the backing; one or more secondary removable liners in contact with the surface of the therapeutic adhesive composition and configured to facilitate application of the heel patch to the heel of a mammal in need thereof, where the secondary removable liners contact less than the total surface of the surface of the therapeutic adhesive composition; and a primary release liner completely covering the adhesive composition and the secondary removable liners, where the primary release liner contains a means for readily separating the primary release liner into a first and a second portion, with each portion remaining in contact with the adhesive composition.

In an exemplary embodiment, the flexible adhesive patch arrangement forms a three-dimensional structure capable of cupping the heel.

In an exemplary embodiment, the means for separating is a perforated pattern or a slit that partially or completely penetrates the primary release liner.

In an exemplary embodiment, the first and the second portions of the primary release liner are different in size.

In an exemplary embodiment, the first and the second portions of the primary release liner are substantially similar in size.

In exemplary embodiments, the area of the primary release liner is equal to or larger than the area of the adhesive composition. In various particular embodiments, the adhesive composition covers 10 to 100% of the surface area of the liner, such as 20 to 100%, such as 25 to 100%, such as 30 to 100%, such as 35 to 100%, such as 40 to 100%, such as 45 to 100%, such as 50 to 100%, such as 60 to 100%, such as 70 to 100%, such as 80 to 100%, such as 90 to 100%.

In an exemplary embodiment, the primary release liner comprises one or more of a polyester film, a polyolefin film, siliconized paper or a plastic laminated paper.

In an exemplary embodiment, the primary release liner has a thickness of about 0.02 to about 0.5 mm.

In an exemplary embodiment, the primary release liner has a thickness of about 0.05 to about 0.3 mm.

In an exemplary embodiment, the backing is porous and/or permeable. In another embodiment, the backing is occlusive. In a particular embodiment, the occlusive backing achieves a moisture vapor transmission rate (MVTR)<100 $g/m^2/24$ h. In another embodiment, the backing is waterproof and breathable and achieves a MVTR>300 $g/m^2/24$ h.

In an exemplary embodiment, the backing has a thickness of about 0.005 mm to about 1.0 mm.

In an exemplary embodiment, the backing has a thickness of about 0.005 mm to about 0.3 mm.

In an exemplary embodiment, the backing comprises polycellulose fibers, polyester fibers, polyurethane fibers, polyolefin fibers, polyamide fibers, cotton fibers, copolyester fibers or any mixture thereof. In another exemplary embodiment, the backing comprises polycellulose film, polyurethane film, polyester film, polyethylene film, polyolefin film or any mixture thereof.

In an exemplary embodiment, the therapeutic adhesive composition comprises one or more of a polyacrylamide, xanthum gum, guar gum, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane, a polyurea, maltodextrin, carboxymethyl cellulose and carboxypropyl cellulose.

In an exemplary embodiment, the therapeutic adhesive composition comprises one or more of a hydrocolloid, a hydrogel, rubber, an acrylic, a silicone and a polyurethane.

In an exemplary embodiment, the therapeutic adhesive composition has a thickness of about 0.01 mm to about 1.5 mm.

In an exemplary embodiment, the therapeutic adhesive composition comprises one or more of an emollient and a descaling (peeling) agent.

In an exemplary embodiment, the descaling agent is salicylic acid and/or urea, and the emollient is a synthetic oil, a plant oil, a wax, an animal oil or a combination thereof.

In an exemplary embodiment, the emollient or the descaling agent is present in an amount of about 0.5 wt. % to about 45 wt. % of the therapeutic adhesive composition.

In an exemplary embodiment, the therapeutic adhesive composition further comprises lactic acid, hydrocortisone, triamcinolone acetonide, betametasone, anthracene, polyethylene, polyvinyl chloride, gelatin, collagen, hexidine, chlorohexamine, sodium chloride, potassium chloride, water, an alcohol or combinations thereof.

In an exemplary embodiment, the alcohol is propylene glycol, glycerol, polyethylene glycol or ethylene glycol.

In an exemplary embodiment, the therapeutic adhesive composition comprises a skin conditioner.

In an exemplary embodiment, the therapeutic adhesive composition comprises an antimicrobial agent.

In an exemplary embodiment, the therapeutic adhesive composition comprises an antiseptic agent.

In an exemplary embodiment, the therapeutic adhesive composition is thicker at the center than at the edges. In a particular embodiment, the thickness of the edge is 0.10 to 0.80, such as 0.2 to 0.7, such as 0.1 to 0.5, such as 0.3 to 0.5, of the thickness of the center.

In an exemplary embodiment, the backing and the therapeutic adhesive composition have an oval shape.

In an exemplary embodiment, the adhesive patch arrangement has a substantially oval shape with a width of about 1 to about 5 inches, such as about 2 to about 5 inches, such as about 2 to about 4 inches, such as about 3 to about 4 inches; and a length of about 3 to about 7 inches, such as about 3 to about 6 inches, such as about 4 to about 6 inches.

In an exemplary embodiment, four secondary removable liners are present in the patch arrangement.

In an exemplary embodiment, the four secondary removable liners appear at the edges of the surface of the therapeutic adhesive composition.

Another aspect of the present invention is a method for attaching the flexible adhesive heel patch of the invention to the heel of a mammal in need thereof, the method comprising: detaching the first portion of the primary release liner from the adhesive patch arrangement to expose a first portion of the adhesive composition surface and the secondary removable liners present underneath the first portion of the primary release liner; attaching the first portion of the adhesive composition to the bottom of the heel; removing the readily detached secondary removable liners uncovered by the detachment of the first portion of the primary release liner; attaching the surface of the adhesive composition uncovered by removal of the secondary removable liners in the previous step to both sides of the heel; detaching the second portion of the primary release liner from the adhesive patch arrangement to expose the remaining portion of the adhesive composition surface and the secondary removable liners present underneath the second portion of the primary release liner; attaching the second portion of the adhesive composition to the back of the heel; removing the secondary removable liners uncovered by the detachment of the second portion of the primary release liner; and attaching the surface of the adhesive composition uncovered by removal of the secondary removable liners in the previous step on top of the patch previously attached to both sides of the heel to complete attachment of the patch to the heel.

In an exemplary embodiment, the mammal is a human.

Another aspect of the present invention is a method for treating or preventing a disorder or condition of the heel of a mammal in need thereof, comprising applying to the affected skin surface an adhesive patch of the invention as described herein for an period of time effective to treat or prevent the heel disorder or condition.

In an exemplary embodiment, the disorder is a cracked heel or a heel fissure.

BRIEF DESCRIPTION OF THE DRAWINGS

The following drawings illustrate specific embodiments of the present invention and are not intended to otherwise narrow the scope of the invention as described herein.

DETAILED DESCRIPTION

Backing Layer

Figure 1:
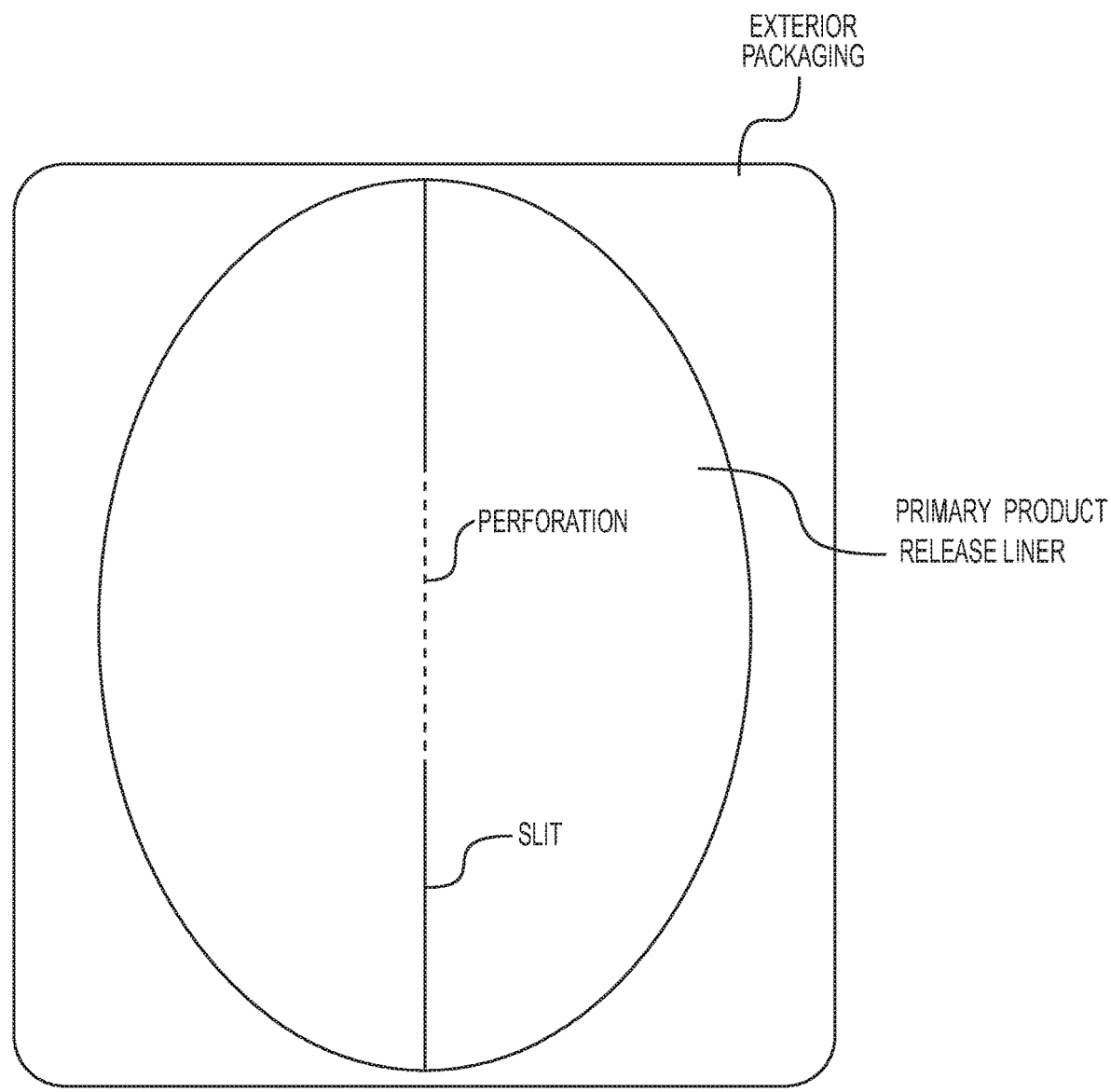
FIG. 1 shows a top view of a particular embodiment of a heel patch of the invention residing in its exterior packaging. The depicted primary release liner protects the underlying therapeutic adhesive composition component of the patch until application of the patch to the skin.
Figure 2:
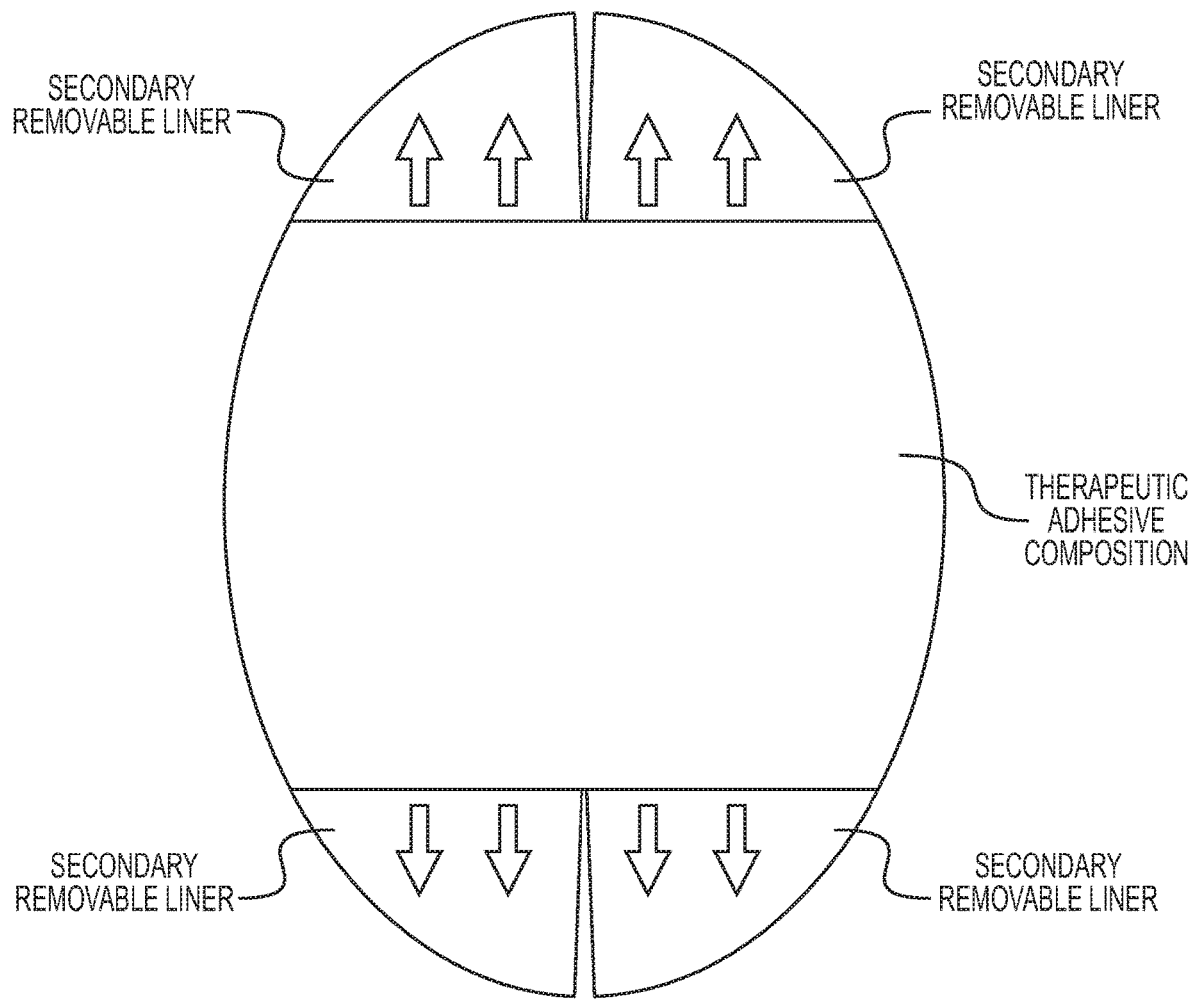
FIG. 2 shows a top view of a particular embodiment of a heel patch of the invention in which the primary release liner has been removed, revealing the underlying therapeutic adhesive composition and four secondary removable liners which facilitate accurate positioning and sealing of the patch on the heel.
Figure 3:
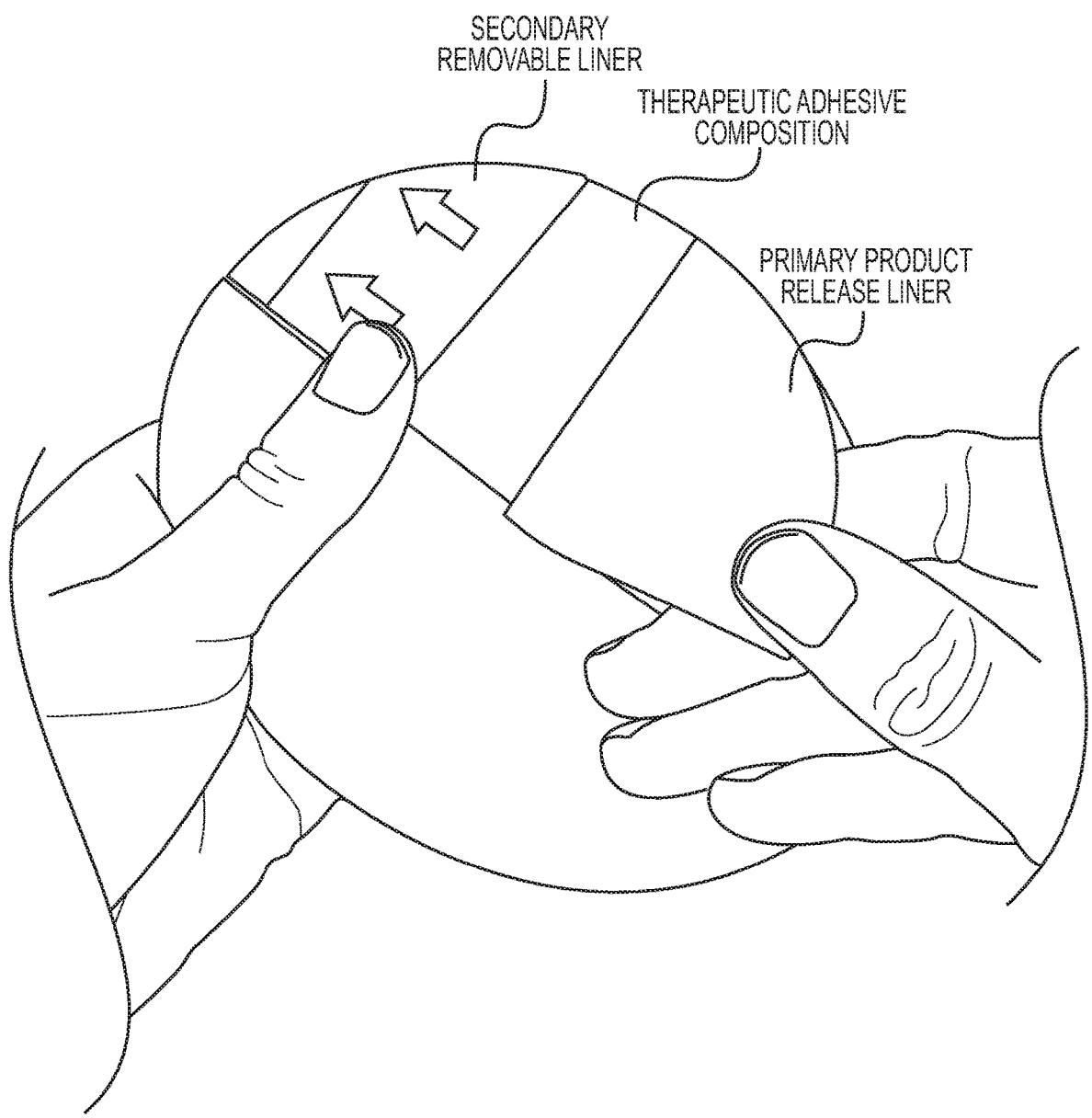
FIG. 3 shows the peeling away of half of the primary release liner of a particular embodiment of a heel patch of the invention, exposing a portion of the therapeutic adhesive composition and a secondary removable liner affixed to the therapeutic adhesive composition.
Figure 4A:
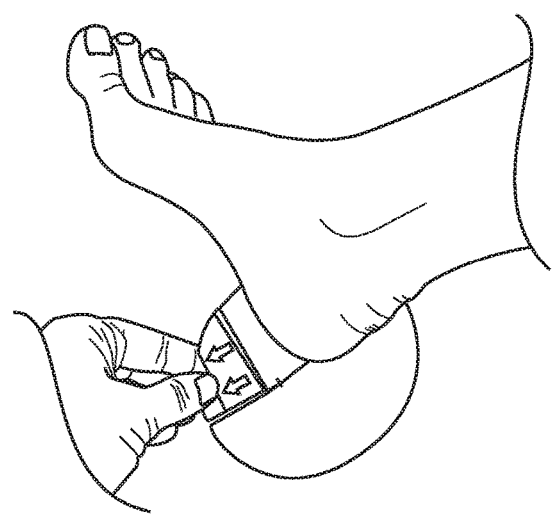
FIGS. 4A, 4B, 4C and 4D show the stepwise application of a particular embodiment of a heel patch of the invention to the heel of a subject that utilizes the secondary removable liners identified by the double arrows.
Figure 4B:
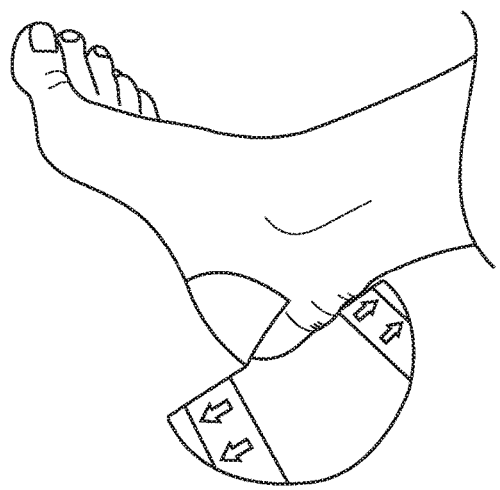
Figure 4C:
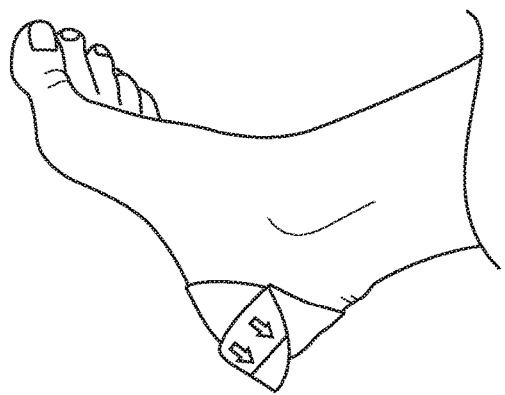
Figure 4D:
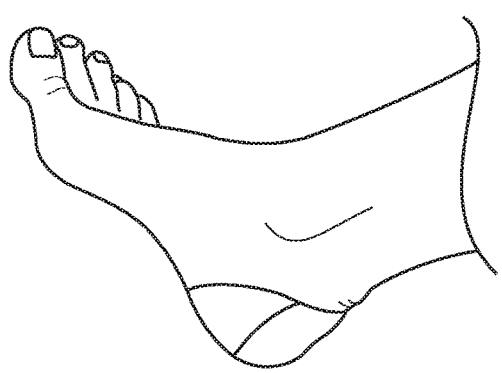
Figure 5:
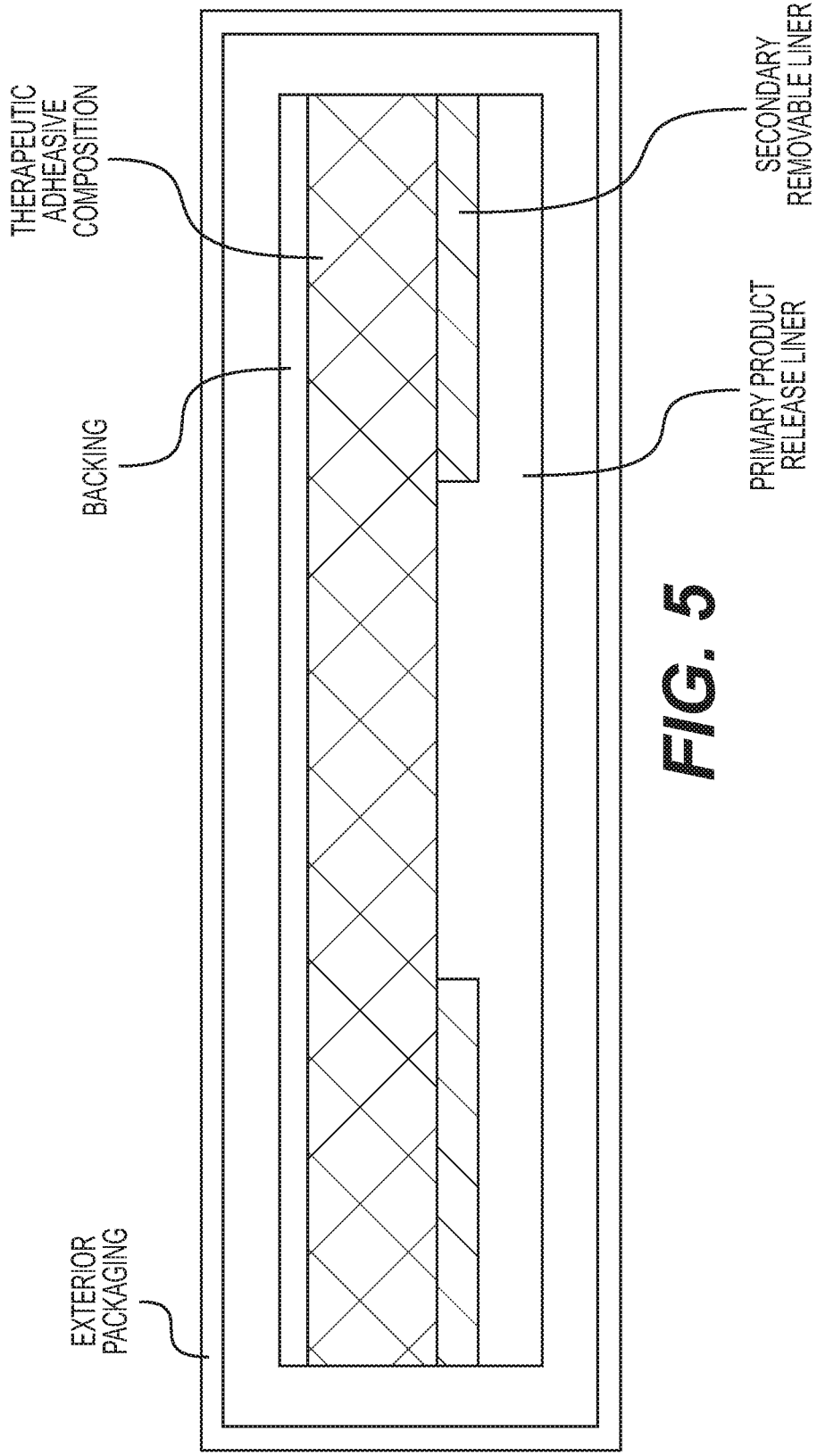
FIG. 5 shows a side view of a particular embodiment of a heel patch arrangement of the invention, consisting of a backing layer, a therapeutic adhesive composition layer, secondary removable liners affixed to the therapeutic adhesive composition and a primary release liner covering both the secondary removable liners and the therapeutic adhesive composition. The heel patch arrangement resides in an exterior package.

The backing layer comprises may comprise any suitable material known for use in the preparation of wound dressings and includes, but is not limited to, a foam, a polyurethane, a polyethylene, a polyester, a polyamide, polycellulose, cotton, or any mixture thereof. In an exemplary embodiment, the backing is flexible, pliable, and/or stretchable. In an exemplary embodiment, the backing contains two sides, a front side and a back side. In an exemplary embodiment, the backing layer is vapor or moisture permeable, but is liquid impermeable. In an exemplary embodiment, the backing layer is continuous (e.g., no holes, perforations or indentations) or is discontinuous (e.g., containing holes, perforations or indentations). In an exemplary embodiment, the backing contains a hydrophobic sizing agent.

The backing layer has a suitable thickness for the intended use. In an exemplary embodiment, the backing layer has a thickness of 0.02 mm to about 1.0 mm, such as 0.03 mm to about 0.8 mm, such as about 0.05 mm to about 0.6 mm, such as about 0.07 mm to about 0.5 mm, such as about 0.1 mm to about 0.5 mm.

In an exemplary embodiment, the backing and the therapeutic adhesive composition have a substantially circular or triangular or rectangular or square or oval shape or the like.

Therapeutic Adhesive Composition

The therapeutic adhesive composition of the present invention consists of or comprises any skin-friendly adhesive composition known for use in medical articles which contact mammalian (e.g., human) skin. Exemplary adhesive compositions may suitably be, but are not limited to, the types disclosed in U.S. 20130152944; 20110105977; U.S. Pat. Nos. 6,495,158; and 9,078,948.

In an exemplary embodiment, the therapeutic adhesive composition is a pressure sensitive therapeutic adhesive composition and may comprise one or more of a polyacrylamide, xanthum gum, guar gum, a hydrogel, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane adhesive, an acrylic adhesive, silicone, a polyurea, maltodextrin, carboxymethyl cellulose, polyisobutylene, rubber, polybutene, carboxypropyl cellulose, polydimethylsiloxane, polystyrene-polybutadiene-polystyrene, polystyrene-polyisoprene-polystyrene, polystyrene-poly(ethylene-butylene)-polystyrene block polymers or any combination thereof.

Exemplary hydrocolloids include, but are not limited to, alginic acid and salts thereof, chitin, chitosan, pectin, cellulose and cellulose derivatives (such as cellulose ethers or cellulose esters), linked or cross-linked carboxyalkylcellulose or hydroxyalkylcellulose, polyvinyl alcohol, polyvinyl pyrrolidone, agar and gelatin.

Other exemplary hydrocolloids include, but are not limited to, polyacrylates or their salts may further be used as a hydrocolloid where the polyacrylate may be present as a homopolymer, copolymer or block polymer.

Suitable active agents present in the therapeutic adhesive composition include, but are not limited to, one or more of an emollient (such as a synthetic oil, a plant oil, a wax, an animal oil or a combination thereof), an antiseptic a descaling (peeling) agent (such as salicylic acid or urea), lactic acid, hydrocortisone, triamcinolone acetonide, betamethasone, anthracene, polyethylene, polyvinyl chloride, gelatin, collagen, hexidine, chlorohexamine, sodium chloride, potassium chloride, water, an alcohol or combinations thereof.

In an exemplary embodiment, the therapeutic adhesive composition comprises a solvent, which includes, but is not limited to, an alcohol (such as a polyhydric alcohol), water, or a combination thereof. In an exemplary embodiment, the polyhydric alcohol is propylene glycol, ethylene glycol, or a combination thereof. In an exemplary embodiment, the solvent is present in an amount of about 0.5 to about 45 wt. %, such as about 0.5 to about 25 wt. %, such as about 5 to about 30 wt. %, of the therapeutic adhesive composition.

In an exemplary embodiment, the adhesive composition is positioned on an entire side of the backing. In an exemplary embodiment, the adhesive composition is positioned on only a portion of an entire side of the backing. In an exemplary embodiment, the adhesive composition is affixed or coated only on the surface of the backing. In an exemplary embodiment, the adhesive composition is partially embedded in at least a portion of the backing.

In an exemplary embodiment, the adhesive composition comprises at least one of glycerin, pectin, a skin conditioner (such as vitamin E, aloe, lanolin, calamine or any combination thereof), an antimicrobial agent (such as antifungal agent), an antiseptic agent (such as iodine or triclosan), an antimicrobial agent (such as erythromycin, tetracycline or cephalosporin), a carotenoid, an analgesic and a hemostyptic in an amount of about 0.01 to about 50 wt. %, such as about 0.1 to 50 wt. %, such as about 1 to 50 wt. %, such as about 5 to about 50 wt. %, such as about 10 to about 50 wt. %, such as about 20 to about 50 wt. %, of the adhesive composition.

In an exemplary embodiment, the therapeutic adhesive composition has a thickness in an amount of 0.01 mm to about 1.5 mm, such as about 0.10 to about 0.60 mm, such as about 0.20 to about 0.50 mm, including other ranges described herein.

In an exemplary embodiment, the present invention also provides for a method for treating or preventing cracked heel (such as heel fissures) in a mammal (e.g., a human) in need or risk thereof, by applying to the heel of the mammal an adhesive patch of the present invention for an period of time effective to treat or prevent the heel disorder. In an exemplary embodiment, the effective period of time is about 10 minutes to about 120 hours, such as about 30 minutes to about 96 hours, such as about 1 to about 96 hours, such as about 6 to about 72 hours, such as about 12 to about 72 hours, such as about 24 to 72 hours, such as about 1 to about 48 hours, such as about 6 to about 48 hours, such as about 12 to about 48 hours, such as about 24 to 48 hours, such as about 1 to about 24 hours, such as about 3 to about 24 hours, such as about 6 to about 24 hours, such as about 12 to 24 hours.

The thickness of the adhesive composition layer of the patch of the present invention may be substantially constant over the surface or the adhesive composition layer or alternatively, the adhesive composition layer may have a thicker portion at the center of the composition compared to the edges of the composition layer—i.e., a beveled edge, where in various particular embodiments, the thickness of the edge is 10% or 20% or 50% or 75% of the thickness of the center.

Any suitable amount of a pressure sensitive adhesive can be present in the therapeutic adhesive composition, provided the amount of pressure sensitive adhesive effectively provides the requisite adhesiveness to the backing and/or the primary release liner and remains stable in the therapeutic adhesive composition over a prolonged period of time. Typically, the therapeutic adhesive composition includes a pressure sensitive adhesive in an amount of about 0.01 wt. % to about 99.99 wt. % of the therapeutic adhesive composition, such as about 0.1 wt. % to about 99.9 wt. %, such as about 1 wt. % to about 99 wt. %, such as about 2 wt. % to about 98 wt. %, such as about 3 wt. % to about 97 wt. %, such as about 5 wt. % to about 95 wt. %, such as about 10 wt. % to about 90 wt. %, such as about 15 wt. % to about 85 wt. %, such as about 20 wt. % to about 80 wt. %, such as about 25 wt. % to about 75 wt. %, such as about 30 wt. % to about 70 wt. %, such as about 40 wt. % to about 60 wt. %.

Primary Release Liner

The primary release liner in the adhesive patch arrangement of the present invention is to coat and protect the adhesive composition of the adhesive patch to prevent the surface of the adhesive composition from being contaminated before attachment. The primary release liner is provisionally attached to the adhesive composition in a readily detachable state, typically requiring only a peeling force to detach.

Suitable compositions of the primary release liners of the present invention include those that are generally known to be used with skin-friendly adhesive compositions, such as primary release liners produced by subjecting a surface of a plastic sheet or a film of a polyolefin (such as polyethylene or polypropylene or a laminate of a plastic film and paper) to a silicone release treatment. In an exemplary embodiment, the primary release liner has a thickness of about 0.01 to about 1.0 mm, such as about 0.03 to about 0.7 mm, such as about 0.07 to about 0.5 mm, such as about 0.1 to about 0.4 mm.

In an exemplary embodiment, the area of the primary release liner is larger than the area of the adhesive patch—i.e., the area of the combined backing and the adhesive composition. In the exemplary embodiment where the primary release liner is larger than the adhesive patch, the portion of the primary release liner that extends beyond the adhesive patch may be held (gripped) by using the fingers of one hand and peeled away from the therapeutic adhesive composition to detach the primary release liner from the therapeutic adhesive composition. In an exemplary embodiment, the primary release liner covering the therapeutic adhesive composition contains a perforated pattern or a slit that allows for facile separation (peeling away) of the primary release liner (in two portions) from the therapeutic adhesive composition.

Slit and/or Perforation

In an exemplary embodiment, the slit that forms the slit line in a single adhesive patch of the present invention partitions the primary release liner into two portions, thus allowing for a tandem (two-step) application of the adhesive patch on the skin of a mammalian subject. In an exemplary embodiment, the primary release liner is cut to a depth in the range of at least 10%, such as 15% or 20% or 30% or 40% or 50% or 60% or 70% or up to 100% of the thickness of the primary release liner to allow ready removal of the primary release liner from the therapeutic adhesive composition.

In addition to a straight line, the slit line may be in any shape that allows for facile separation of the primary release liner into multiple portions. For example, the shape may be a curve, a zigzag line, an arc shape, a wave shape or a saw-tooth shape.

In an exemplary embodiment, the primary release liner is perforated to also facilitate a tandem (two-step) application of the adhesive patch on the skin of a mammalian subject. In addition to a straight line, the perforation may be in any shape that allows for facile separation of the primary release liner into multiple portions. For example, the shape may be a curve, a zigzag line, an arc shape, a wave shape or a saw-tooth shape.

In an exemplary embodiment, the primary release liner contains a combination of a perforated section and a slit.

Secondary Removable Liners

The secondary removable liners in the adhesive patch arrangement of the present invention coat and protect the adhesive composition of the adhesive patch to prevent the surface of the adhesive composition from being contaminated before attachment. In particular, the secondary removable liners are removed subsequent to the primary release liner during application of the adhesive patch and are integral to the ease of application of the adhesive patch of the invention to the heel of a subject in need thereof and to the snug fit of the patch once the patch is applied. As with the primary release liner, the secondary removable liners are provisionally attached to the surface of the adhesive composition in a readily detachable state, requiring only a peeling force to detach. There is no limit on the number of secondary removable liners present on the surface of the adhesive composition. In an exemplary embodiment, there are four secondary removable liners present on the surface of the adhesive composition. In an exemplary embodiment, the secondary removable liners are substantially transparent. In an exemplary embodiment, the secondary removable liners are embossed with arrows to facilitate ease of application of the adhesive patch. In an exemplary embodiment, the secondary removable liners are the same or similar in composition to that of the backing.

EXAMPLES

The following non-limiting exemplary formulations illustrate suitable adhesive compositions for use in the therapeutic adhesive compositions of the present invention.

Example 1

(a) 5 to 20 wt % or 5 to 15 wt % or 10 to 15 wt % of an elastomer;
(b) 1 to 10 wt % or 2 to 10 wt % or 4 to 10 wt % of a mineral oil plasticizer;
(c) 20 to 60 wt % or 25 to 55 wt % or 30 to 55 wt % or 35 to 45 wt % of a tackifier; and
(d) 20 to 60 wt % or 25 to 50 wt % or 30 to 45 wt % of an absorbent,
where the total weight percent of components (a) through (d) is 100%.

In exemplary embodiments of the above formulation of Example 1, the elastomer is selected from the group consisting of Kraton SEBS, Kraton SIS, Kraton SBS and mixtures thereof; the mineral oil plasticizer is selected from the group consisting of mineral oil, plant oil, hydrogenated botanical oil and mixtures thereof; the tackifier is selected from the group consisting of acrylic resin, c5 tackifier, hydrogenated hydrocarbon resin and mixtures thereof; and the absorbent is selected from the group consisting of carboxymethylcelluose, gelatin, SAP super absorbents and mixtures thereof.

Example 2

(a) 10 to 15 wt % of mineral oil;
(b) 25 to 50 wt % or 30 to 40 wt % of carboxymethylcellulose;
(c) 3 to 15 wt % or 5 to 10 wt % of KRATON® 1161; and
(d) 25 to 45 wt % or 30 to 40 wt % of ARKON® P115,
where the total weight percent of components (a) through (d) is 100%.

Example 3

(a) 3 to 10 wt % or 5 to 10 wt % of mineral oil;
(b) 25 to 50 wt % or 30 to 40 wt % of carboxymethylcellulose;
(c) 10 to 25 wt % or 15 to 20 wt % of KRATON® 1161; and
(d) 25 to 55 wt % or 35 to 45 wt % of FORAL® 85,
where the total weight percent of components (a) through (d) is 100%.

Example 4

(a) 35 to 65 wt % or 45 to 55 wt % of mineral oil; and
(b) 35 to 65 wt % or 45 to 55 wt % of carboxymethylcellulose,
where the total weight percent of components (a) and (b) is 100%.

Example 5

(a) 20 to 45 wt % or 30 to 40 wt % of alpha linolenic acid;
(b) 15 to 40 wt % or 20 to 35 wt % of carboxymethylcellulose;
(c) 20 to 45 wt % or 25 to 40 wt % of KRATON®; and
(d) 10 to 25 wt % or 15 to 20 wt % FORAL® 85,
where the total weight percent of components (a) through (d) is 100%.

Example 6

(a) 1 to 15 wt % or 5 to 10 wt % of myristic acid;
(b) 20 to 50 wt % or 30 to 40 wt % of carboxymethylcellulose;
(c) 10 to 30 wt % or 15 to 25 wt % of KRATON®; and
(d) 20 to 55 wt % or 35 to 50 wt % of FORAL® 85, where the total weight percent of components (a) through (d) is 100%.

Example 7

(a) 20 to 45 wt % or 25 to 40 wt % of a 1:1:1 mixture of mineral oil and alpha linolenic acid and myristic acid;
(b) 10 to 35 wt % or 15 to 30 wt % of carboxymethylcellulose;
(c) 15 to 40 wt % or 25 to 40 wt % of KRATON®; and
(d) 10 to 30 wt % or 15 to 25 wt % of FORAL® 85,
where the total weight percent of components (a) through (d) is 100%.

Example 8

(a) 35 to 65 wt % or 40 to 55 wt % of a 1:2:1 mixture of mineral oil and alpha linolenic and myristic acid;
(b) 15 to 40 wt % or 20 to 45 wt % of carboxymethylcellulose;
(c) 5 to 30 wt % or 5 to 20 wt % of KRATON®; and
(d) 1 to 20 wt % or 10 to 15% of FORAL® 85, where the total weight percent of components (a) through (d) is 100%.

All patents and other publications cited herein are incorporated by reference in their entireties.

The invention claimed is:
1. A flexible adhesive heel patch arrangement comprising:
a flexible adhesive patch comprising:
a backing having two sides;
a therapeutic adhesive composition coated on at least a portion of one side of the backing;
secondary removable liners in contact with the surface of the therapeutic adhesive composition and configured to facilitate application of the heel patch to the heel of a mammal, where the secondary removable liners contact less than the total surface of the surface of the therapeutic adhesive composition; and
a primary release liner completely covering the therapeutic adhesive composition and the secondary removable liners, where the primary release liner contains a means for readily separating the primary release liner into a first and a second portion, with each portion remaining in contact with the adhesive composition.
2. The adhesive heel patch arrangement according to claim 1, wherein the means for separating is a perforated pattern or a slit that partially or completely penetrates the primary release liner.
3. The adhesive patch arrangement according to claim 1, wherein the area of the primary release liner is equal to or larger than the area of the therapeutic adhesive composition.
4. The adhesive patch arrangement according to claim 1, wherein the primary release liner comprises one or more of a polyester film, a polyolefin film or a plastic laminated paper.
5. The adhesive patch arrangement according to claim 1, wherein the primary release liner has a thickness of about 0.02 mm to about 0.5 mm.
6. The adhesive patch arrangement according to claim 1, wherein the backing has a thickness of about 0.005 mm to about 1.0 mm.
7. The adhesive patch arrangement according to claim 1, wherein the backing comprises polycellulose fibers, polyester fibers, polyurethane fibers, polyolefin fibers, polyamide fibers, cotton fibers, copolyester fibers, a polycellulose film, a polyurethane film, a polyester film, a polyethylene film, a polyolefin film or any mixture thereof.

8. The adhesive patch arrangement according to claim 1, wherein the therapeutic adhesive composition comprises one or more of a polyacrylamide, xanthum gum, guar gum, a hydrocolloid, a starch, a vinyl acetate copolymer, polyvinyl pyrrolidone, polyvinyl alcohol, polyethylene oxide, a polyacrylate, polymaleic acid, polymaleic anhydride, a polyurethane, a polyurea, maltodextrin, carboxymethyl cellulose, carboxypropyl cellulose, a hydrocolloid, a hydrogel, rubber, an acrylic, a silicone, a polyurethane, an emollient, a descaling agent, lactic acid, hydrocortisone, triamcinolone acetonide, betametasone, anthracene, polyethylene, polyvinyl chloride, gelatin, collagen, hexidine, chlorohexamine, sodium chloride, potassium chloride, water, an alcohol, a skin conditioner, an antimicrobial agent, or an antiseptic agent.
9. The adhesive patch arrangement according to claim 1, wherein the therapeutic adhesive composition has a thickness of about 0.1 mm to about 3 mm.
10. The adhesive patch arrangement according to claim 1, wherein the therapeutic adhesive composition is thicker at the center than at the edges.
11. The adhesive patch arrangement according to claim 1, wherein the arrangement has an oval shape.
12. The adhesive patch arrangement according to claim 11, having a width of 2 to 5 inches and a length of 3 to 7 inches.
13. The adhesive patch arrangement according to claim 1, wherein the patch arrangement comprises four secondary removable liners that appear at edges of the surface of the therapeutic adhesive composition.
14. A method for attaching the flexible adhesive heel patch arrangement according to claim 1 to the heel of a mammal, the method comprising:
detaching the first portion of the primary release liner from the adhesive patch arrangement to expose a first portion of the adhesive composition surface and the secondary removable liners present underneath the first portion of the liner;
attaching the first portion of the adhesive composition to the bottom of the heel;
removing the secondary removable liners uncovered by the detachment of the first portion of the primary release liner;
attaching the surface of the adhesive composition uncovered by removal of the secondary removable liners in the previous step to both sides of the heel;
detaching the second portion of the primary release liner from the adhesive patch arrangement to expose the remaining portion of the adhesive composition surface and the secondary removable liners present underneath the second portion of the primary release liner;
attaching the second portion of the adhesive composition to the back of the heel;
removing the secondary removable liners uncovered by the detachment of the second portion of the primary release liner; and
attaching the surface of the adhesive composition uncovered by removal of the secondary removable liners in the previous step on top of the patch previously attached to both sides of the heel to complete attachment of the patch to the heel.
15. The method according to claim 14, wherein the mammal is a human.
16. The method according to claim 14, wherein the means for separating is a perforated pattern or a slit that partially or completely penetrates the primary release liner.

17. The method according to claim 14, wherein the area of the primary release liner is equal to or larger than the area of the therapeutic adhesive composition.

18. A method for treating or preventing a disorder or condition of the heel of a mammal, comprising applying to the affected skin surface the flexible adhesive patch arrangement according to claim 1 for a period of time effective to treat or prevent the heel disorder or condition.

19. The method according to claim 18, wherein the disorder or condition is a heel fissure or a cracked heel.

20. The method of claim 18 wherein the mammal is a human.

\* \* \* \* \*